(12) United States Patent
Kao et al.

(10) Patent No.: US 8,427,151 B2
(45) Date of Patent: Apr. 23, 2013

(54) METHOD AND APPARATUS FOR BRAIN PERFUSION MAGNETIC RESONANCE IMAGES

(75) Inventors: Yi-Hsuan Kao, Taipei (TW); Mu-Huo Teng, Taipei (TW); Wen-Yan Zheng, Taichung County (TW); Yu-Fen Chen, Taichung (TW)

(73) Assignee: National Yang-Ming University, Taipei (TW)

( * ) Notice: Subject to any disclaimer, the term of this patent is extended or adjusted under 35 U.S.C. 154(b) by 359 days.

(21) Appl. No.: 13/007,357

(22) Filed: Jan. 14, 2011

(65) Prior Publication Data

US 2012/0184843 A1    Jul. 19, 2012

(51) Int. Cl.
*G01V 3/00*    (2006.01)

(52) U.S. Cl.
USPC .......................................................... 324/307

(58) Field of Classification Search .......... 324/300–322; 600/407–445
See application file for complete search history.

(56) References Cited

U.S. PATENT DOCUMENTS

| | | | |
|---|---|---|---|
| 5,262,945 A * | 11/1993 | DeCarli et al. ................. | 600/410 |
| 5,560,360 A * | 10/1996 | Filler et al. ..................... | 600/408 |
| 5,617,861 A * | 4/1997 | Ross et al. ..................... | 600/410 |
| 5,812,691 A * | 9/1998 | Udupa et al. .................. | 382/128 |
| 6,546,275 B2 | 4/2003 | Carroll | |
| 7,020,578 B2 | 3/2006 | Sorensen et al. | |
| 7,069,068 B1 | 6/2006 | Ostergaard | |
| 7,512,435 B2 | 3/2009 | Wu et al. | |
| 7,519,412 B2 * | 4/2009 | Mistretta ....................... | 600/407 |
| 7,580,737 B2 | 8/2009 | Wintermark et al. | |
| 7,672,790 B2 * | 3/2010 | McGraw et al. ................ | 702/19 |
| 8,301,223 B2 * | 10/2012 | Lee et al. ....................... | 600/410 |
| 2011/0018537 A1 * | 1/2011 | Warntjes ........................ | 324/309 |
| 2012/0323112 A1 * | 12/2012 | Jokerst et al. ................. | 600/420 |

OTHER PUBLICATIONS

Kao et al., "Hemodynamic Segmentation of MR Brain Perfusion Images Using Independent Component Analysis, Thresholding, and Bayesian Estimation," Magnetic Resonance in Medicine, 2003, pp. 885-894, vol. 49.

Sonka et al., "Handbook of Medical Imaging, vol. 2, Medical Image Processing and Analysis," SPIE—The International Society for Optical Engineering, Bellingham, Washington, 2000, pp. 101-120.

Simon et al., "A novel method to derive separate gray and white matter cerebral blood flow measures from MR imaging of acute ischemic stroke patients," Journal of Cerebral Blood Flow & Metabolism, 2005, pp. 1236-1243, vol. 25.

(Continued)

*Primary Examiner* — Brij Shrivastav
(74) *Attorney, Agent, or Firm* — Muncy, Geissler, Olds & Lowe, PLLC

(57) ABSTRACT

The present invention discloses a method and apparatus for brain perfusion magnetic resonance imaging (MRI) technique with the removal of cerebrospinal fluid (CSF) pixels. This invention utilizes a CSF/brain-contrast-enhanced image, wherein the CSF/brain-contrast-enhanced image is defined as the signal difference between CSF and brain matter divided by a standard deviation of air background random noise is larger than 3, acquired from the subject's brain, and applies a segmentation technique to remove the CSF pixels. After removing the CSF pixels on parametric images, the extent of brain tissue with delayed perfusion can be better identified. By using a good region of interest enclosing the correct delayed-perfusion region, the measurement on the tissue volume and perfusion parameters would be more accurate than the area contaminated by CSF pixels.

52 Claims, 5 Drawing Sheets

Gradient-echo EPI, effective TR/TR/TE = infinity/1000/40

Inversion-recovery, gradient-echo, EPI, TR/TE/TI = 3500/40/300 ms

OTHER PUBLICATIONS

Otsu, "A Threshold Selection Method from Gray-Level Histograms," IEEE Transactions on Systems, Man, and Cybernetics, vol. SMC-9, No. 1, Jan. 1979, pp. 62-66.

Shafait et al., "Efficient Implementation of Local Adaptive Thresholding Techniques Using Integral Images," In Proc. SPIE Document Recognition and Retrieval XV, Jan. 2008, pp. 101-106.

Kao et al., "Removal of CSF Pixels on Brain MR Perfusion Images Using First Several Images and Otsu's Thresholding Technique," Magnetic Resonance in Medicine, 2010, pp. 743-748, vol. 64.

Martel et al., "Extracting parametric images from dynamic contrast-enhanced MRI studies of the brain using factor analysis," Medical Image Analysis, 2001, pp. 29-39, vol. 5.

Teng et al., "Automatic processing of MR perfusion with removal of CSF signal contamination," National Yang Ming University, Taipei, Taiwan, R.O.C., Jan. 17, 2010.

\* cited by examiner

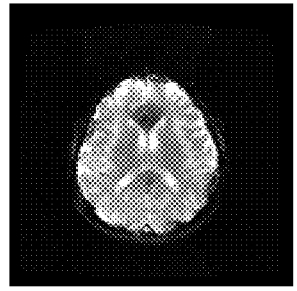

FIG.2(a),
Gradient-echo EPI,
effective TR/TR/TE = infinity/1000/40

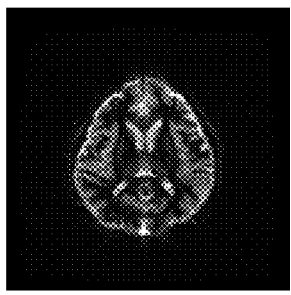

FIG.2(b),
Inversion-recovery, gradient-echo, EPI,
TR/TE/TI = 3500/40/300 ms

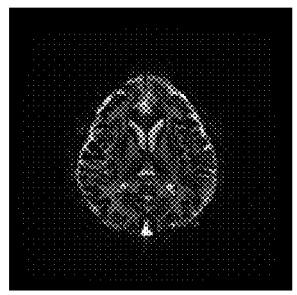

FIG.2(c),
Inversion-recovery, gradient-echo, EPI,
TR/TE/TI = 3500/40/400 ms

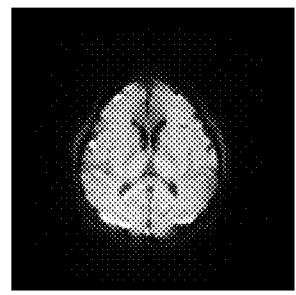

FIG.2(d),
Inversion-recovery, gradient-echo, EPI,
TR/TE/TI=12000/40/2200 ms

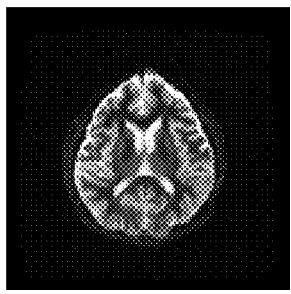

FIG.2(e),
Inversion-recovery, spin-echo, EPI,
TR/TE/TI = 3500/40/300 ms

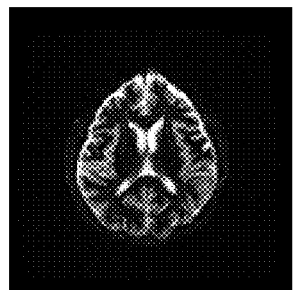

FIG.2(f),
Inversion-recovery, spin-echo, EPI,
TR/TE/TI = 3500/40/400 ms

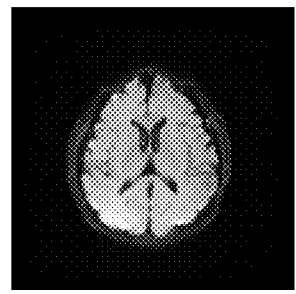

FIG.2(g),
Inversion-recovery, spin-echo, EPI,
TR/TE/TI=12000/40/2200 ms

Figure 2

METHOD AND APPARATUS FOR BRAIN PERFUSION MAGNETIC RESONANCE IMAGES

BACKGROUND OF THE INVENTION

1. Field of the Invention

The present invention relates generally to a method and apparatus for brain perfusion magnetic resonance imaging (MRI) technique, and more particularly, to a method and apparatus for brain perfusion MRI technique with removal of cerebrospinal fluid (CSF) pixels using a CSF/brain-contrast-enhanced image and a segmentation technique.

2. Background

Brain perfusion MRI technique is used for the diagnosis of cerebrovascular diseases such as stroke and stenosis. Traditional tracer kinetic models for intravascular agents can be extended to dynamic susceptibility contrast MRI data to calculate cerebral blood volume (CBV), cerebral blood flow (CBF), and tracer mean transit time (MTT). According to the central volume theorem, MTT=CBV/CBF. In a dynamic-susceptibility-contrast perfusion MRI study, a bolus of contrast agents is injected through an antecubital vein and a series of dynamic images are acquired from the patient's brain to record the passage of contrast agents. Parametric images such as time to peak (TTP) of the concentration-time curve and MTT can be calculated from the dynamic images to reveal local perfusion at brain tissues. Tissues with hyperintensity on either TTP or MTT images have delayed blood perfusion and they are at risk of infarction. These two parametric images are valuable for the diagnosis and treatment planning of cerebrovascular diseases. However, CSF also appears hyperintensity on these two parametric images and CSF may interfere with quantitative measurements on the extent of tissues with delayed perfusion. Therefore, the identification and removal of CSF pixels on perfusion parametric images can improve the measurements on the area of tissue with delayed perfusion.

U.S. Pat. No. 6,546,275, issued to Carroll et al. entitled "Determination of the arterial input function in dynamic contrast-enhanced MRI" discloses that a contrast-enhanced MRI time course study of the brain is performed and images are produced which indicate hemodynamic parameters such as CBF, CBV and MTT. An arterial input function required to quantitatively measure the hemodynamic parameters is automatically produced.

U.S. Pat. No. 7,020,578, issued to Sorensen et al. entitled "Method for evaluating novel, stroke treatments using a tissue risk map" discloses that a method of evaluating stroke treatments includes generating a risk map indicative of the probability of tissue infarction on voxel-by-voxel basis and selecting a probability range for evaluating the therapeutic effect of the treatment. In one particular embodiment, tissue having a fifty percent probability of tissue infarction is selected. A treatment that has a reduced level of overall actual infarction as compared to the predicted value is indicative of therapeutic effect.

U.S. Pat. No. 7,069,068, issued to Ostergaard et al. entitled "Method for determining haemodynamic indices by use of tomographic data" discloses that haemodynamic indices of an organ or a part of tissue are determined from a time series of tomographic data obtained by means of MRI. Maps of indices are produced, being significant of the dynamics of the capillary tissue flow acquired during rapid bolus injection of a tracer that stays mainly intravascular. The method may be used for evaluating the efficacy of a drug on an organ, or for obtaining information of the likelihood of recovery of an organ or part of tissue upon or during a period of insufficient vascular supply or during the progression of a chronic disease. The method may be used for discriminating between relevant therapy of an organ.

U.S. Pat. No. 7,512,435, issued to Wu et al. entitled "Delay-compensated calculation of tissue blood flow" discloses that methods for computing perfusion parameters are described. The methods are typically used to analyze MR images and other image data and to calculate tissue perfusion parameters such as CBF in the brain or in tissues in other organs such as the heart. The methods employ a block-circulant matrix for deconvolving the perfusion parameters from the image data.

U.S. Pat. No. 7,580,737, issued to Wintermark et al. entitled "Method and apparatus for determining treatment for stroke" discloses that a method and apparatus for evaluating acute stroke patients and for determining whether a stroke patient will benefit from the use of thrombolysis therapy includes obtaining measurements of the CBF and CBV of the brain of a stroke patient, determining ischemic areas of the brain where the ischemic areas comprise the measurements of CBF which are less than a first value and creating a penumbra-infarct map of the ischemic areas of the brain using the measurements. The infarct area corresponds to the area of the brain where CBV is less than a second value. The penumbra area corresponds to the area of the brain where CBV is greater than this second value. The method also includes determining a ratio of penumbra size to the total of penumbra size and infarct size. When the ratio is greater than a predetermined value, the stroke patient is a candidate for thrombolysis therapy.

However, the above disclosures do not effectively remove the CSF pixels on brain perfusion parametric images to improve the measurements on the area of tissue with delayed perfusion. According above problems, it needs a method and apparatus to overcome the disadvantage of the prior art.

BRIEF SUMMARY OF THE INVENTION

It is an objective of the present invention to provide a method for analyzing brain perfusion MR images with removal of CSF pixels.

It is another objective of the present invention to provide an apparatus for analyzing brain perfusion MR images with removal of CSF pixels.

To achieve the above objective, the present invention provides a method for removing CSF pixels on a brain perfusion parametric image of a subject, with a MRI system, the subject being administered with a contrast agent. The method comprises the steps of: a) acquiring a series of dynamic MR images from the subject's brain, wherein the dynamic MR images comprises at least a signal of CSF and at least a signal of brain matter; b) calculating a brain perfusion parametric image from the dynamic images; c) acquiring a CSF/brain-contrast-enhanced image, wherein the CSF/brain-contrast-enhanced image is defined as the signal difference between CSF and brain matter divided by a standard deviation of air background random noise is larger than 3, from the subject's brain; d) applying a segmentation method to the CSF/brain-contrast-enhanced image with or without the use of other images of the subject's brain for identifying a plurality of CSF pixels; and e) removing the CSF pixels identified in the step d), when displaying the brain perfusion parametric image calculated in the step b).

To achieve another objective, the present invention provides an apparatus for removing CSF pixels on a brain perfusion parametric image of a subject, with a MRI system, the subject being administered with a contrast agent. The apparatus comprises a) first acquiring mean for acquiring a series of dynamic MR images from the subject's brain, wherein the dynamic MR images comprises at least a signal of CSF and at least a signal of brain matter; b) calculating mean for calculating a brain perfusion parametric image from the dynamic images; c) second acquiring mean for acquiring a CSF/brain-contrast-enhanced image, wherein the CSF/brain-contrast-enhanced image is defined as the signal difference between CSF and brain matter divided by a standard deviation of air background random noise is larger than 3, from the subject's brain; d) applying mean for applying a segmentation method to the CSF/brain-contrast-enhanced image with or without the use of other images of the subject's brain for identifying a plurality of CSF pixels; and e) removing mean for removing the CSF pixels identified from the applying mean, when displaying the brain perfusion parametric image calculated in the calculating mean.

The present invention provides a segmentation technique to removal CSF pixels on perfusion parametric images. The present invention also provides a technique to compensate the CSF/brain-contrast-enhanced image for the inhomogeneity of excitation radiofrequency field in the medical imaging system.

This invention utilizes the CSF/brain-contrast-enhanced image to remove the CSF pixels. After removing the CSF pixels on parametric images, the extent of brain tissue with delayed perfusion can be better identified.

By using a good region of interest enclosing the correct delayed-perfusion region, the measurement on the tissue volume, TTP, and MTT, as well as other perfusion parameters such as CBV and CBF would be more accurate than the area contaminated by CSF pixels.

For all of the new methods, software, and systems, the subject can be a human or animal, e.g., a mammal, such as a domesticated mammal, such as a dog, cat, horse, cow, goat, or pig. The new methods also work for other animals that have circulatory systems.

These and many other advantages and features of the present invention will be readily apparent to those skilled in the art from the following drawings and detailed descriptions.

BRIEF DESCRIPTION OF THE DRAWINGS

All the objectives, advantages, and novel features of the invention will become more apparent from the following detailed description when taken in conjunction with the accompanying drawings.

FIG. 2(a) shows a gradient-echo (GE), echo-planar image (EPI) acquired with an effective repetition time (TR)=infinity. This is the first image acquired in a dynamic scan used for acquiring perfusion MR images. In the dynamic scan, the scan parameters were set to TR=1000 ms and echo time (TE)=40 ms. This image is usually discarded in a perfusion study because signal equilibrium is not reached.

FIG. 2(b) shows an inversion-recovery, GE, EPI acquired with TR/TE/TI=3500/40/300 ms, where TI is the inversion time.

FIG. 2(c) shows an inversion-recovery, GE, EPI acquired with TR/TE/TI=3500/40/400 ms.

FIG. 2(d) shows an inversion-recovery, GE, EPI acquired with TR/TE/TI=12000/40/2200 ms.

FIG. 2(e) shows an inversion-recovery, spin-echo (SE), EPI acquired with TR/TE/TI=3500/40/300 ms.

FIG. 2(f) shows an inversion-recovery, SE, EPI acquired with TR/TE/TI=3500/40/400 ms.

FIG. 2(g) shows an inversion-recovery, SE, EPI acquired with TR/TE/TI=12000/40/2200 ms.

FIG. 3(a) is the first GE EPI acquired from a subject with effective TR/TR/TE=infinity/1000/40 ms. FIG. 3(b) is the second GE EPI acquired with TR/TE=1000/40 ms. FIG. 3(c) is a two-dimensional histogram (or called scatter plot) for the two images displayed in (a) and (b). By using the principle component analysis technique, the output images are shown in FIG. 3(d) and FIG. 3(e). FIG. 3(f) is the scatter plot of the two output images. The contrast between CSF and brain matter is improved in the two output images in FIG. 3(d) and FIG. 3(e), as compared with the two input images in FIG. 3(a) and FIG. 3(b).

FIG. 4(a) is the scatter plot of two input images. The two input images are the output images of principle component analysis shown in FIGS. 3(d) and 3(e). By using a fuzzy c-means clustering technique, two clusters are identified on the scatter plot as shown in FIG. 4(b). The two black crosses are the centroids of the two clusters. By assigning each pixel to the tissue type with the highest probability, two output images are generated to represent brain matter in FIG. 4(c) and CSF in FIG. 4(d).

DETAILED DESCRIPTION OF THE INVENTION

Figure 1:
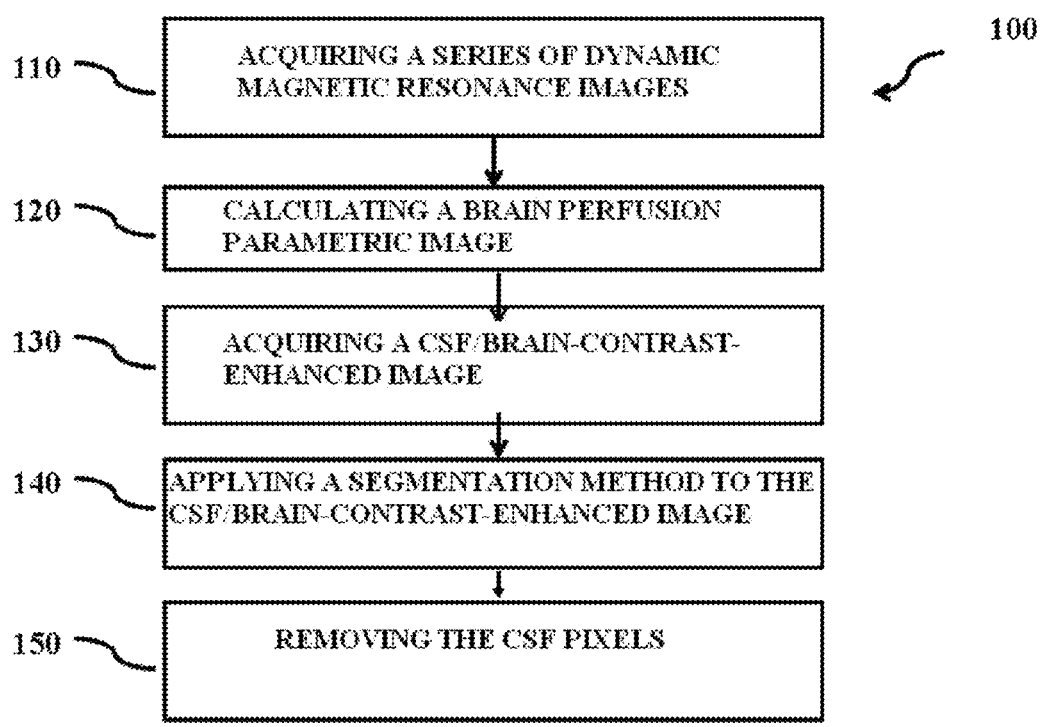
FIG. 1 is a general method of the first embodiment outlining a flowchart to produce a brain perfusion parametric image with the removal of CSF pixels.

FIG. 1 is a general method 100 of the first embodiment outlining a flowchart for removing CSF pixels on a brain perfusion parametric image of a subject, with a magnetic resonance imaging system, the subject being administered with a contrast agent. The method comprises the steps of:

Step 110) acquiring a series of dynamic MR images from the subject's brain, wherein the dynamic MR images comprises at least a signal of CSF and at least a signal of brain matter;

Step 120) calculating a brain perfusion parametric image from the dynamic images; Step 130) acquiring a CSF/brain-contrast-enhanced image, wherein the CSF/brain- contrast-enhanced image is defined as the signal difference between CSF and brain matter divided by a standard deviation of air background random noise is larger than 3, from the subject's brain;

Step 140) applying a segmentation method to the CSF/brain-contrast-enhanced image with or without the use of other images of the subject's brain for identifying a plurality of CSF pixels; and Step 150) removing the CSF pixels identified in step 140), when displaying the brain perfusion parametric image calculated in step 120).

In the step 110, it is acquiring a series of dynamic MR images from the subject's brain, wherein the dynamic MR images comprises at least a signal of CSF and a signal of brain matter. Method 100 first acquires at least N dynamic parametric images, with a medical imaging system, such as MRI, by monitoring the injection of a bolus of a contrast agent. In some embodiments, method 100 acquires dynamic susceptibility contrast MR images using either SE EPI or GE EPI during the passage of contrast agent with the use an MR imaging-compatible power injector. Typically the bolus of a gadolinium-based contrast agent with a dosage of 0.1 mM/kg body weight is followed by a comparable volume of normal saline injected at the same rate. Using such pulse sequences, datasets of 7 slices over 70 (Namely, N=70) dynamic parametric images are typically obtained.

The step 120 is calculating a brain perfusion parametric image from the dynamic images. The calculated brain perfusion parameter image is at least one of CBV, CBF, relative CBV, relative CBF, TTP, and MTT images.

The step 130 is acquiring a CSF/brain-contrast-enhanced image, wherein the CSF/brain-contrast-enhanced image is defined as the signal difference between CSF and brain matter divided by a standard deviation of air background random noise is larger than 3, from the subject's brain. Moreover, acquiring the CSF/brain-contrast-enhanced images can be performed either separately or continuously with the dynamic images.

The CSF/brain-contrast-enhanced image can be acquired from a subject's brain using the following magnetic resonance imaging pulse sequences, but not limited to:

(1) A imaging pulse sequence with an effective repetition time (TR) longer than 2 seconds, in which the signal of the CSF is bright and the signal of the brain matter is dark;

(2) An inversion-recovery imaging pulse sequence with an inversion time (TI) between 0.1 and 0.7 seconds, in which the signal of the CSF is bright and the signal of the brain matter is dark;

(3) An inversion-recovery imaging pulse sequence with a TI between 1.8 and 2.4 seconds, in which the signal of the CSF is dark and the signal of the brain matter is bright;

The above mentioned images, such as the CSF/brain-contrast-enhanced image can be acquired by using, but not limited: 1) SE; 2) GE; 3) GE EPI; 4) SE EPI techniques. FIGS. 2(a)-2(g) illustrate CSF/brain-contrast-enhanced images acquired by using different imaging techniques in the step 130.

FIG. 2(a) shows a GE, EPI acquired with an effective TR=infinity. This is the first image acquired in a dynamic scan used for acquiring perfusion MR images. In the dynamic scan, the scan parameters were set to TR=1000 ms and TE=40 ms. This image is usually discarded in a perfusion study because signal equilibrium is not reached. On this image, the signal of the CSF is bright and the signal of the brain matter is dark.

FIG. 2(b) shows an inversion-recovery, GE, EPI acquired with TR/TE/TI=3500/40/300 ms. On this image, the signal of the CSF is bright and the signal of the brain matter is dark.

FIG. 2(c) shows an inversion-recovery, GE, EPI acquired with TR/TE/TI=3500/40/400 ms. On this image, the signal of the CSF is bright and the signal of the brain matter is dark.

FIG. 2(d) shows an inversion-recovery, GE, EPI acquired with TR/TE/TI=12000/40/2200 ms. On this image, the signal of the CSF is dark and the signal of the brain matter is bright.

FIG. 2(e) shows an inversion-recovery, SE, EPI acquired with TR/TE/TI=3500/40/300 ms. On this image, the signal of the CSF is bright and the signal of the brain matter is dark.

FIG. 2(f) shows an inversion-recovery, SE, EPI acquired with TR/TE/TI=3500/40/400 ms. On this image, the signal of the CSF is bright and the signal of the brain matter is dark.

FIG. 2(g) shows an inversion-recovery, SE, EPI acquired with TR/TE/TI=12000/40/2200 ms. On this image, the signal of the CSF is dark and the signal of the brain matter is bright.

The step 140 is applying a segmentation method to the CSF/brain-contrast-enhanced image with or without the use of other images of the subject's brain for identifying a plurality of CSF pixels containing the signals of CSF.

It is noted many segmentation techniques, such as factor analysis technique, clustering technique, thresholding technique, can be used in the step 140. The following used segmentation techniques are explained:

Factor analysis technique

In factor analysis, the observed signals are modeled as linear combinations of latent source factors plus noise. By using statistical methods, the source factors can be estimated. The most commonly used technique is principle component analysis (PCA). In PCA, the source factors are sorted according to their variance, from the largest to the smallest. In PCA, the source factors are called principle components. Components with small variances are not as important as those components with large variances. The principle components are orthogonal, and as a result, the inner product between any two principle components is zero. Another useful technique is the independent component analysis (ICA). In this technique, the source factors are required to be statistically independent and they are called independent components. A statistical measure such as entropy is used to describe the statistical independence.

Both PCA and ICA can be applied to analyze a plurality of images of the same anatomy, but with different contrast. For example, PCA is applied to brain perfusion MR images for identifying arterial-phase and venous-phase images. Paper titled as "Extracting parametric images from dynamic contrast-enhanced MRI studies of the brain using factor analysis." by Martel AL et al. in Med Image Anal 2001; 5:29-39. is used as reference. The ICA technique is also applied to brain perfusion MR images for segmenting tissues with different blood supply patterns. Paper titled as "Hemodynamic segmentation of MR brain perfusion images using independent component analysis, thresholding, and Bayesian estimation." by Kao Y H et al in Magnetic Resonance in Medicine 2003; 49: 885-894. is used as reference.

The difference between two techniques is that both the output images and the signal-time curves are required to be orthogonal in the PCA calculation. However, in ICA calculation, only the output independent-component images are required to be statistical independent. There is no orthogonality requirement on the output signal-time curves.

Figure 3:
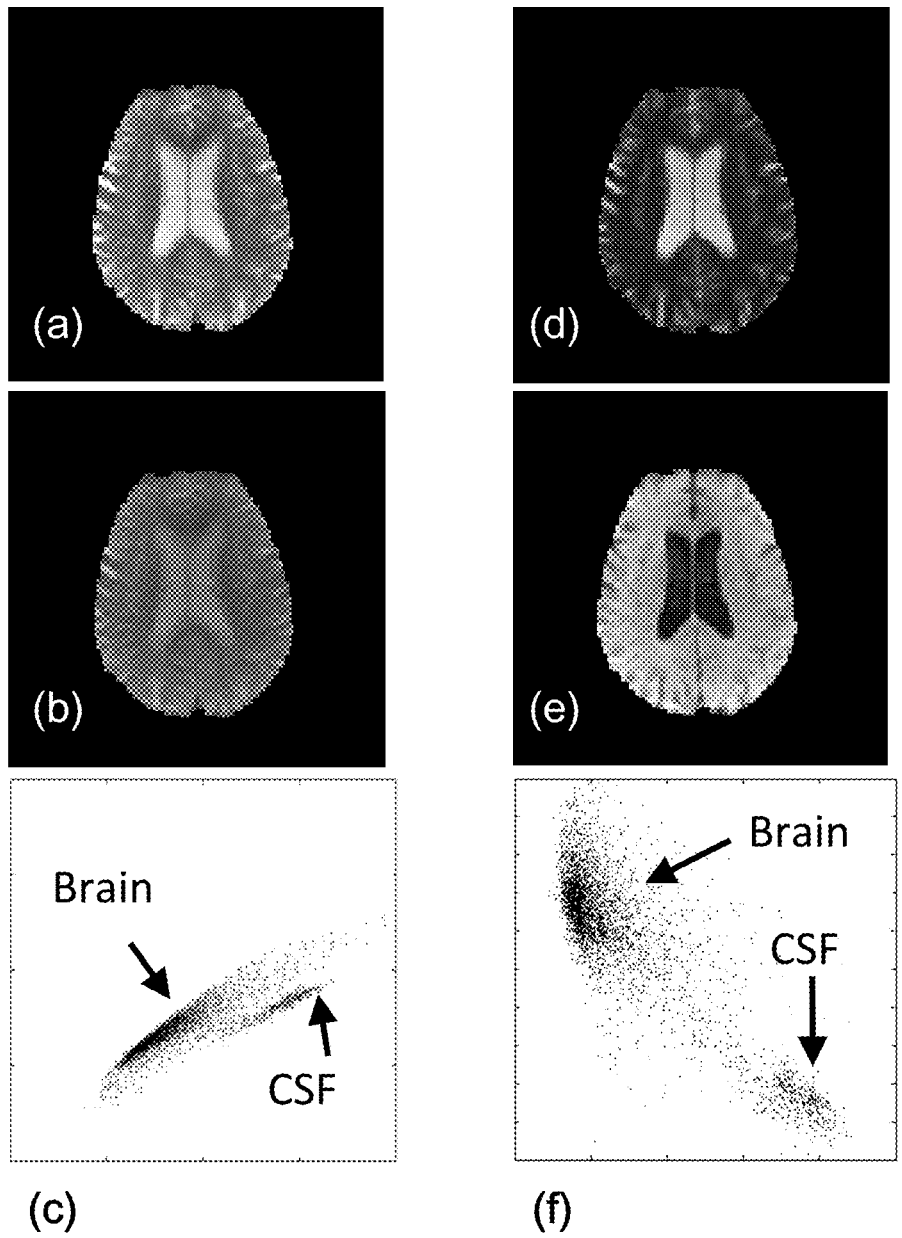
FIG. 3 is an example of the principle component analysis technique for the step 140 of the present invention.

FIG. 3 is an example of the principle component analysis technique for the step 140 of the present invention. FIG. 3(a) is the first GE EPI acquired with effective TR/TR/TE=infinity/1000/40 ms. FIG. 3(b) is the second GE EPI acquired with TRITE=1000/40 ms. FIG. 3(c) is a two-dimensional histogram (or called scatter plot) for the two images displayed in (a) and (b), for pixels inside the bone. FIG. 3(c) displays the scatter plot of signals for pixels inside the bone, including both CSF and brain pixels. The horizontal axis is the signal on the first EPI and the vertical axis is the signal on the second EPI.

By using the PCA technique, the output images are shown in FIG. 3(d) and FIG. 3(e). FIG. 3(f) is the scatter plot of the two output images processed by using principle component analysis, for the same pixels. The horizontal axis is the signal on the first output image shown in FIG. 3(d), and the vertical axis is the signal on the second output image shown in FIG. 3(e). It is shown that the contrast between CSF and brain matter is improved in the two output images in FIG. 3(d) and FIG. 3(e), as compared with the two input images in FIG. 3(a) and FIG. 3(b).

Clustering technique

Cluster technique can be used to assign pixels to different tissue types (or called clusters). In each cluster, pixels have similar signal intensities on a single image or a plurality of images. For example, a clustering technique can be used to assign pixels to three tissue types, based on the signal intensities on two input images of the same anatomy. A two-dimensional histogram, or called scatter plot, can be generated from the two input images. Three centroids, representing the three different tissue clusters, can be initially assigned on the scatter plot. A distance measure is used to describe the similarity between a pixel and a centroid on the scatter plot.

Commonly used clustering techniques include: 1) unsupervised technique such as k-means and fuzzy c-means; and 2) supervised technique such as Bayes classifier and Markov random field. Book titled as "Handbook of Medical Imaging, Volume 2. Medical Image Processing and Analysis." by J. Michael Fitzpatrick (Editor) and Milan Sonka (Editor). SPIE press, Bellingham, Wash., USA. Year 2000, page: 101-120. and paper titled as "A novel method to derive separate gray and white matter cerebral blood flow measures from MR imaging of acute ischemic stroke patients." by J. E. Simon et al. in Journal of Cerebral Blood Flow & Metabolism 2005; 25: 1236-1243. are used as a reference. In the k-means clustering technique, each pixel is assigned to the tissue type whose centroid is nearest on the scatter plot. The centroid is calculated as the averaged coordinate values on the scatter plot, for points included in the cluster. By repeatedly calculating the centroids and distance measures, the clusters will move on the two-dimensional histogram until a convergence criterion is met. (Note: k-means is explained in the Medical Imaging book, page 107.)

In the fuzzy c-means clustering, each pixel is assigned probabilities of belonging to different tissue types. Using the example of two input images and three tissues types mentioned above, three probabilities are assigned to each pixel and the sum of these three probabilities is one. The centroid of a cluster is the weighted averaged coordinate values, for all pixels on the scatter plot, and the weighting is the calculated probability. Iteration process is used and the three centroids are moving on the scatter plot, until a convergence criterion is met. By using the final three probabilities, each pixel can be assigned to a tissue type with the largest probability. (Note: fuzzy c-means is explained in the Medical Imaging book, page 108.)

The Bayes classifier is also called the maximum likelihood classifier. A priori probability is assumed for each tissue type when calculating the probability for a pixel belonging to various tissue types. For the Markov random field technique, the spatial relationship between neighboring pixels is included in the probability calculation. (Note: Bayes classifier is explained in the Medical Imaging book, page 108-109.) (Note: Markov random field is explained in the Medical Imaging book, page 118-119.)

Figure 4:
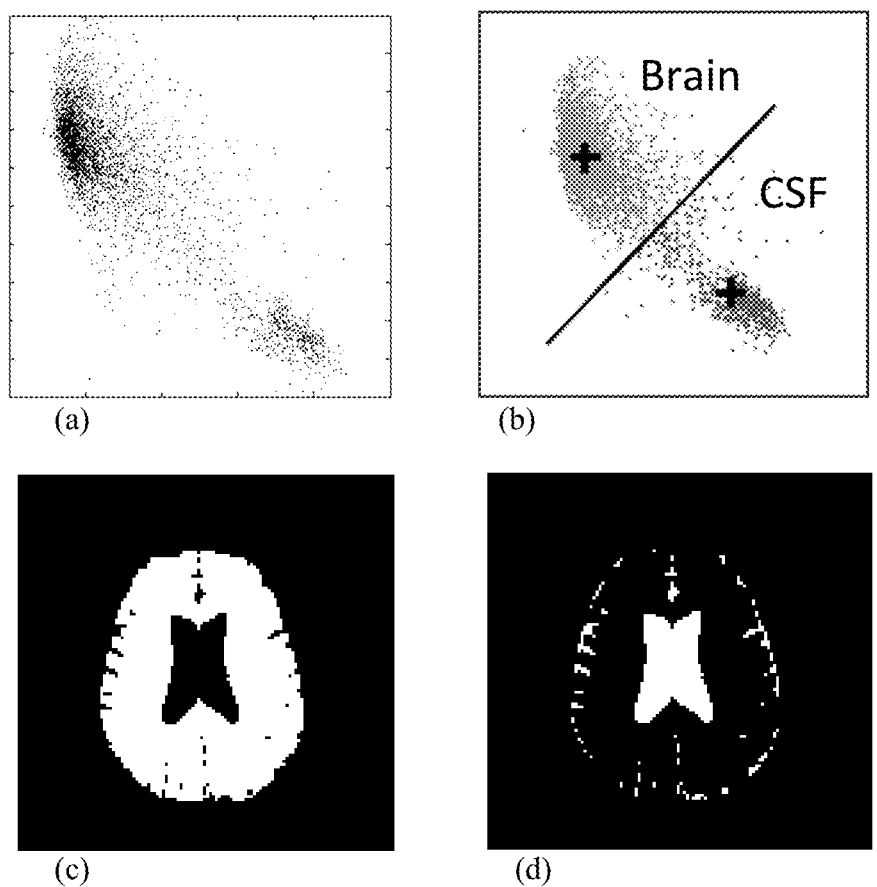
FIG. 4 is an example of the fuzzy c-means clustering technique for the step 140 of the present invention.

FIG. 4 is an example of the fuzzy c-means clustering technique for the step 140 of the present invention. FIG. 4(a) is the scatter plot of two input images. The two input images are the output images of principle component analysis shown in FIGS. 3(d) and 3(e). By using a fuzzy c-means clustering technique, two clusters are identified on the scatter plot as shown in FIG. 4(b). The two black crosses are the centroids of the two clusters. By assigning each pixel to the tissue type with the highest probability, two output images are generated to represent brain matter in FIG. 4(c) and CSF in FIG. 4(d).

Thresholding technique

The thresholding technique can be used to generate binary images from a gray-level image. A threshold can be chosen as either the mean or median value on the image. Pixel with an intensity higher (or lower) than the threshold is assign to the 'target' type. Pixel with an intensity lower (or higher) than the threshold is assign to the 'background' type. For example, if CSF is bright and brain matter is dark on an image. A pixel with intensity higher than the threshold is assigned to CSF pixel. A pixel with intensity lower than the threshold is assigned to brain-matter pixel.

More sophisticated techniques are developed for choosing a threshold. In Otsu's technique, a signal histogram of the image is plotted and statistical measures such as means and variances are calculated for choosing an appropriate threshold. Paper titled as "Threshold selection method from gray-level histogram." by Otsu, N. in IEEE Transactions on Systems Man and Cybernetics, 1979; 9:62-66. is used as reference.

Color images and a plurality of images with different contrast also can be segmented by using the thresholding technique. For example, one can apply different thresholds to different contrast images. Pixels being identified as 'target' on all images are assigned to 'target' type.

In the technique described above, only one threshold is applied to one image for generating binary images. However, there are occasions that signal intensity on an image is modulated by a slow varying non-uniformity. Local thresholding techniques are developed for producing binary images. In the local thresholding techniques, the signal histogram for a local area (for example a 7×7 box) around a single pixel is generated. An appropriate threshold is determined from the local area. The signal on this specific pixel is compared with the local threshold for determining whether this pixel should be assigned to "target' or 'background'. This process is repeated for all pixels on the image. Paper titled as F. Shafait, D. Keysers, and T. M. Breuel. Efficient implementation of local adaptive thresholding techniques using integral images. In Proc. SPIE Document Recognition and Retrieval XV, pages 101-106, San Jose, Calif., USA, January 2008. is used as reference.

The step 150 is removing the CSF pixels identified in step 140), when displaying the brain perfusion parametric image calculated in step 120).

In this step, the pixels included in the CSF mask are removed from the parametric images. The parametric image is at least one of CBV, CBF, relative CBV, relative CBF, MTT, and TTP. The above description examines the theory and analysis for one of the parametric images, which can be also found in the cited reference:. U.S. Pat. No. 7,512,435, issued to Wu et al. entitled "Delay-compensated calculation of tissue blood flow". By computing such parameters for each pixel, maps of perfusion parameters are calculated to assist in clinical diagnosis. With the removal of CSF pixels, the volume of delayed-perfusion brain parenchyma can be better visualized and the interference from the CSF can be avoided.

Moreover, the inhomogeneity of excitation radiofrequency field usually causes the spatially dependent signal variation. Therefore, in this invention, the disclosed invention uses an image division technology to generate ratio images to compensate for the spatially dependent signal variation caused by the inhomogeneity of excitation radiofrequency field. By applying an appropriate signal threshold to the ratio images, CSF pixels can be well identified and then removed from the parametric images. Thus, the step 140 can further comprises the step of compensating the CSF/brain-contrast-enhanced image to be an inhomogeneity compensated image for the inhomogeneity of excitation radiofrequency field. The step of compensating is achieved by using a reference image, wherein the reference image is calculated by averaging the Pth to the Qth dynamic images, and P and Q are both integers, wherein P is equal to six and Q is equal to ten. Moreover, the thresholding technique and the clustering technique disclosed above are also applied to the inhomogeneity compensated image. Paper titled as "Removal of CSF pixels on brain MR perfusion images using first several images and Otsu's thresholding technique." by Kao Y H, et al. in Magnetic Resonance in Medicine 2010;64:743-748. is used as reference.

Implementation

In some embodiments, the steps described above are implemented in computer programs using standard programming techniques or directly in an apparatus. Therefore, the apparatus for removing CSF pixels on a brain perfusion parametric image of a subject, with a magnetic resonance imaging system, the subject being administered with a contrast agent, comprises: a) first acquiring mean for acquiring a series of dynamic MRI from the subject's brain, wherein the dynamic MRI comprises at least a signal of CSF and at least a signal of brain matter; b) calculating mean for calculating a brain perfusion parametric image from the dynamic images; c) second acquiring mean for acquiring a CSF/brain-contrast-enhanced image, wherein the CSF/brain-contrast-enhanced image is defined as the signal difference between CSF and brain matter divided by a standard deviation of air background random noise is larger than 3, from the subject's brain; d) applying mean for applying a segmentation method to the CSF/brain-contrast-enhanced image with or without the use of other images of the subject's brain for identifying a plurality of CSF pixels; and e) removing mean for removing the CSF pixels identified from the applying mean, when displaying the brain perfusion parametric image calculated in the calculating mean.

Such an apparatus or programs are designed to execute on programmable computers each comprising an electronic processor, a data storage system (including memory and/or storage elements). In some embodiments, the program code is applied to control the acquisition of the image data, such as MRI data, using a pulse sequence stored in the software. In other embodiments, the code is applied directly to acquired data (e.g., MRI data from the imager) to perform the functions described herein and generate output information (e.g. CBF, MTT, or CBV), which is applied to one or more output devices. In yet other embodiments, the program code is applied to acquisition of the data by controlling a MR imager and to the subsequent analysis described herein. Each such computer program can be implemented in a high-level procedural or object-oriented programming language, or an assembly or machine language. Furthermore, the language can be a compiled or interpreted language. Each such computer program can be stored on a computer readable (machine-readable) storage medium (e.g., CD ROM or magnetic diskette) that when read by a computer can cause the processor in the computer to perform the analysis described herein.

The software using the disclosed method of the present invention can be manufactured and/or sold, e.g., by medical imaging system manufacturers either as part of the original software supplied to new MRI or other imaging device, or as a later add-on "upgrade" to existing imaging devices. The software can also be made and/or sold by independent software manufacturers directly to users of such MRI or other imaging devices.

Figure 5:
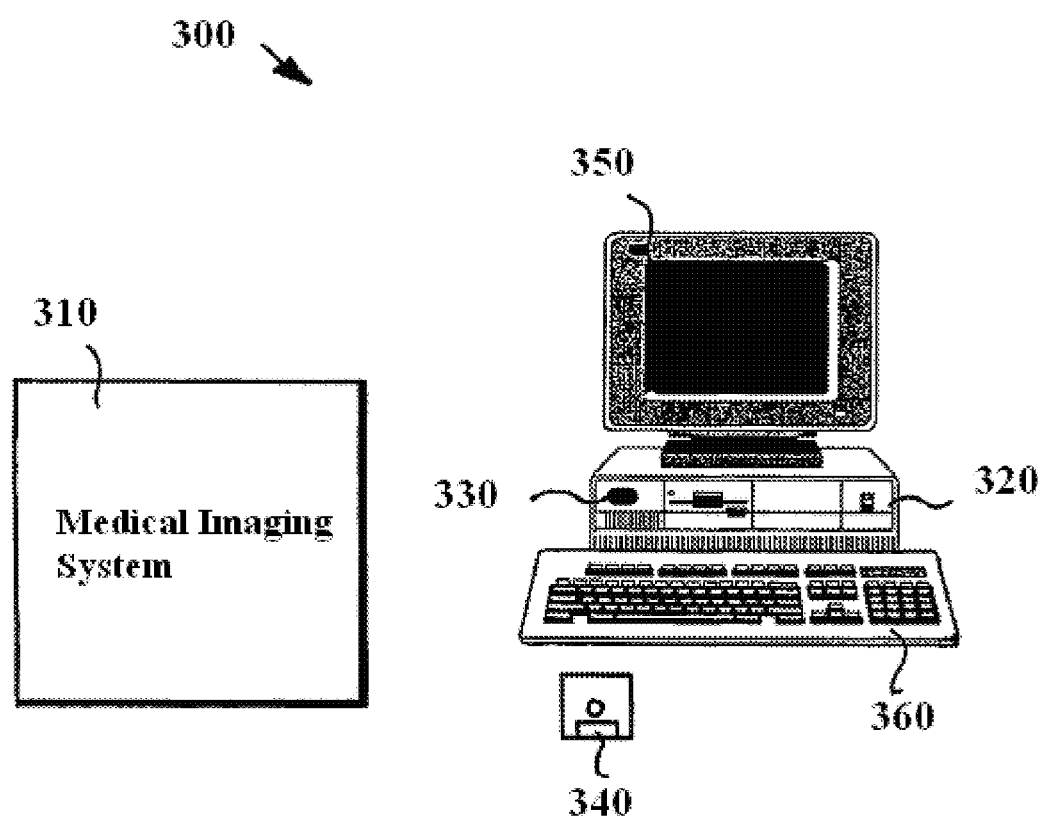
FIG. 5 is a schematic diagram of an imaging system that can incorporate the new methods embodied in software.

In this invention, the disclosed method can be implemented as a software or a hardware, used in imaging systems. For example, as shown in FIG. 5, the imaging system 300 can include an medical imaging system 310, such as a magnetic resonance imaging system, a processor 320, such as a person computer or microprocessor, associated with the imaging device 310; and a memory 330 coupled to the processor 320 that contains the software using the disclosed method of the present invention, or reads the software from a computer-readable storage device 340. The memory 330 contains the new software of the present invention that, when executed, causes the processor 320 to: a) acquiring a series of dynamic MRI from the subject's brain, wherein the dynamic MRI comprises at least a signal of CSF and at least a signal of brain matter; b) calculating a brain perfusion parametric image from the dynamic images; c) acquiring a CSF/brain-contrast-enhanced image, wherein the CSF/brain-contrast-enhanced image is defined as the signal difference between CSF and brain matter divided by a standard deviation of air background random noise is larger than 3, from the subject's brain; d) applying a segmentation method to the CSF/brain-contrast-enhanced image with or without the use of other images of the subject's brain for identifying a plurality of CSF pixels; and e) removing the CSF pixels identified in the step d), when displaying the brain perfusion parametric image calculated in the step b).

The imaging system 300 can also include an output device 350 for displaying the blood perfusion parameter, such as a monitor, e.g., CRT, or printer. The system can also include an input device 360, such as a keyboard or mouse, for providing data or instructions to the system.

Although the invention has been explained in relation to several preferred embodiments, the accompanying drawings and the following detailed descriptions are the preferred embodiment of the present invention. It is to be understood that the following disclosed descriptions will be examples of present invention, and will not limit the present invention into the drawings and the special embodiment.

The functions and the advantages of the present invention have been shown. Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. A method for removing cerebrospinal fluid (CSF) pixels on a brain perfusion parametric image of a subject, with a magnetic resonance imaging system, the subject being administered with a contrast agent, comprising the steps of:
   a) acquiring a series of dynamic magnetic resonance images from the subject's brain wherein the dynamic magnetic resonance images comprises at least a signal of CSF and at least a signal of brain matter;
   b) calculating a brain perfusion parametric image from the dynamic images;
   c) acquiring a CSF/brain-contrast-enhanced image, wherein the CSF/brain-contrast-enhanced image is defined as the signal difference between CSF and brain matter divided by a standard deviation of air background random noise is larger than 3, from the subject's brain;
   d) applying a segmentation method to the CSF/brain-contrast-enhanced image with or without the use of other images of the subject's brain for identifying a plurality of CSF pixels containing the signal of CSF; and
   e) removing the CSF pixels identified in the step d), when displaying the brain perfusion parametric image calculated in the step b).

2. The method as claimed in claim 1, wherein in the step c), acquiring the CSF/brain-contrast-enhanced images can be performed either separately or continuously with the dynamic images.

3. The method as claimed in claim 1, wherein acquiring the CSF/brain-contrast-enhanced image can be performed using a pulse sequence with an effective repetition time (TR) longer than 2 seconds, in which CSF is bright on the images.

4. The method as claimed in claim 2, wherein acquiring the CSF/brain-contrast-enhanced image can be performed using a pulse sequence with an effective repetition time (TR) longer than 2 seconds, in which CSF is bright on the images.

5. The method as claimed in claim 1, wherein acquiring the CSF/brain-contrast-enhanced image can be performed using an inversion-recovery pulse sequence with an inversion time used to reduce the signal of CSF, in which CSF is dark on the image.

6. The method as claimed in claim 2, wherein acquiring the CSF/brain-contrast-enhanced image can be performed using an inversion-recovery pulse sequence with an inversion time used to reduce the signal of CSF, in which CSF is dark on the image.

7. The method as claimed in claim 1, wherein acquiring the CSF/brain-contrast-enhanced image can be performed using an inversion-recovery pulse sequence with an inversion time used to reduce the signals of brain matter, in which brain matter is dark on the image.

8. The method as claimed in claim 2, wherein acquiring the CSF/brain-contrast-enhanced image can be performed using an inversion-recovery pulse sequence with an inversion time used to reduce the signals of brain matter, in which brain matter is dark on the image.

9. The method as claimed in claim 1, wherein in the step d), a thresholding technique is used in the segmentation method.

10. The method as claimed in claim 1, wherein in the step d), a clustering technique is used in the segmentation method.

11. The method as claimed in claim 1, wherein in the step e), a factor analysis technique is used in the segmentation method.

12. The method as claimed in claim 11, wherein a thresholding technique is applied to an output image of the factor analysis technique.

13. The method as claimed in claim 11, wherein a clustering technique is applied to an output images of the factor analysis technique.

14. The method as claimed in claim 1, wherein the step d) further comprises the step of compensating the CSF/brain-contrast-enhanced image to be an inhomogeneity compensated image for the inhomogeneity of excitation radiofrequency field.

15. The method as claimed in claim 14, wherein the step of compensating is achieved by using a reference image, wherein the reference image is calculated by averaging the Pth to the Qth dynamic images, and P and Q are both integers.

16. The method as claimed in claim 14, wherein a thresholding technique is applied to the inhomogeneity compensated image.

17. The method as claimed in claim 14, wherein a clustering technique is applied to the inhomogeneity compensated image.

18. The method as claimed in claim 1, wherein in the step b), the calculated brain perfusion parameter image is at least one of cerebral blood volume (CBV), cerebral blood flow (CBF), relative cerebral blood volume (rCBV), relative cerebral blood flow (rCBF), time-to-peak (TTP), and mean transit time (MTT) images.

19. The method as claimed in claims 9, wherein the thresholding technique is one of global thresholding technique, or local thresholding technique.

20. The method as claimed in claims 12, wherein the thresholding technique is one of global thresholding technique, or local thresholding technique.

21. The method as claimed in claims 16, wherein the thresholding technique is one of global thresholding technique, or local thresholding technique.

22. The method as claimed in claim 10, wherein the clustering technique is one of k-mean clustering technique, or fuzzy c-means clustering technique, or Bayes classifier technique, or Markov random field technique.

23. The method as claimed in claim 13, wherein the clustering technique is one of k-mean clustering technique, or fuzzy c-means clustering technique, or Bayes classifier technique, or Markov random field technique.

24. The method as claimed in claim 17, wherein the clustering technique is one of k-mean clustering technique, or fuzzy c-means clustering technique, or Bayes classifier technique, or Markov random field technique.

25. The method as claimed in claim 11, wherein the factor analysis technique is one of principle component analysis or independent component analysis.

26. The method as claimed in claim 15, wherein P is equal to six and Q is equal to ten.

27. An apparatus for removing cerebrospinal fluid (CSF) pixels on a brain perfusion parametric image of a subject, with a magnetic resonance imaging system, the subject being administered with a contrast agent, comprising:
   a) first acquiring mean for acquiring a series of dynamic magnetic resonance images from the subject's brain, wherein the dynamic magnetic resonance images comprises at least a signal of CSF and at least a signal of brain matter;
   b) calculating mean for calculating a brain perfusion parametric image from the dynamic images;
   c) second acquiring mean for acquiring a CSF/brain-contrast-enhanced image, wherein the CSF/brain-contrast-enhanced image is defined as the signal difference between CSF and brain matter divided by a standard deviation of air background random noise is larger than 3, from the subject's brain;
   d) applying mean for applying a segmentation method to the CSF/brain-contrast-enhanced image with or without the use of other images of the subject's brain for identifying a plurality of CSF pixels containing the signal of CSF; and
   e) removing mean for removing the CSF pixels identified from the applying mean, when displaying the brain perfusion parametric image calculated in the calculating mean.

28. The apparatus as claimed in claim 27, wherein mean for acquiring the CSF/brain-contrast-enhanced images can be performed either separately or continuously with the dynamic images.

29. The apparatus as claimed in claim 27, wherein mean for acquiring the CSF/brain-contrast-enhanced image can be performed using a pulse sequence with an effective repetition time (TR) longer than 2 seconds, in which CSF is bright on the images.

30. The apparatus as claimed in claim 28, wherein mean for acquiring the CSF/brain-contrast-enhanced image can be performed using a pulse sequence with an effective repetition time (TR) longer than 2 seconds, in which CSF is bright on the images.

31. The apparatus as claimed in claim 27, wherein mean for acquiring the CSF/brain-contrast-enhanced image can be performed using an inversion-recovery pulse sequence with an inversion time used to reduce the signal of CSF, in which CSF is dark on the image.

32. The apparatus as claimed in claim 28, wherein mean for acquiring the CSF/brain-contrast-enhanced image can be performed using an inversion-recovery pulse sequence with an inversion time used to reduce the signal of CSF, in which CSF is dark on the image.

33. The apparatus as claimed in claim 27, wherein mean for acquiring the CSF/brain-contrast-enhanced image can be performed using an inversion-recovery pulse sequence with an inversion time used to reduce the signals of brain matter, in which brain matter is dark on the image.

34. The apparatus as claimed in claim 28, wherein mean for acquiring the CSF/brain-contrast-enhanced image can be performed using an inversion-recovery pulse sequence with an inversion time used to reduce the signals of brain matter, in which brain matter is dark on the image.

35. The apparatus as claimed in claim 27, wherein a thresholding technique is used in the segmentation method.

36. The apparatus as claimed in claim 27, wherein a clustering technique is used in the segmentation method.

37. The apparatus as claimed in claim 27, wherein a factor analysis technique is used in the segmentation method.

38. The apparatus as claimed in claim 37, wherein a thresholding technique is applied to an output image of the factor analysis technique.

39. The apparatus as claimed in claim 37, wherein a clustering technique is applied to an output images of the factor analysis technique.

40. The apparatus as claimed in claim 27, wherein mean for applying a segmentation method compensates the CSF/brain-contrast-enhanced image to be an inhomogeneity compensated image for the inhomogeneity of excitation radiofrequency field.

41. The apparatus as claimed in claim 40, wherein mean for applying a segmentation method compensates the CSF/brain-contrast-enhanced image by using a reference image, wherein the reference image is calculated by averaging the Pth to the Qth dynamic images, and P and Q are both integers.

42. The apparatus as claimed in claim 40, wherein a thresholding technique is applied to the inhomogeneity compensated image.

43. The apparatus as claimed in claim 40, wherein a clustering technique is applied to the inhomogeneity compensated image.

44. The apparatus as claimed in claim 27, wherein in the step b), the calculated brain perfusion parameter image is at least one of cerebral blood volume (CBV), cerebral blood flow (CBF), relative cerebral blood volume (rCBV), relative cerebral blood flow (rCBF), time-to-peak (TTP), and mean transit time (MTT) images.

45. The apparatus as claimed in claims 35, wherein the thresholding technique is one of global thresholding technique, or local thresholding technique.

46. The apparatus as claimed in claims 38, wherein the thresholding technique is one of global thresholding technique, or local thresholding technique.

47. The apparatus as claimed in claims 42, wherein the thresholding technique is one of global thresholding technique, or local thresholding technique.

48. The apparatus as claimed in claim 36, wherein the clustering technique is one of k-mean clustering technique, or fuzzy c-means clustering technique, or Bayes classifier technique, or Markov random field technique.

49. The apparatus as claimed in claim 39, wherein the clustering technique is one of k-mean clustering technique, or fuzzy c-means clustering technique, or Bayes classifier technique, or Markov random field technique.

50. The apparatus as claimed in claim 43, wherein the clustering technique is one of k-mean clustering technique, or fuzzy c-means clustering technique, or Bayes classifier technique, or Markov random field technique.

51. The apparatus as claimed in claim 37, wherein the factor analysis technique is one of principle component analysis or independent component analysis.

52. The apparatus as claimed in claim 41, wherein P is equal to six and Q is equal to ten.

\* \* \* \* \*